United States Patent [19]

Tallen et al.

[11] Patent Number: 4,966,844

[45] Date of Patent: Oct. 30, 1990

[54] METHOD FOR MICROBIAL CELL KILLING

[75] Inventors: Michael J. Tallen; Dennis M. Fenton, both of Thousand Oaks, Calif.

[73] Assignee: Amgen, Thousand Oaks, Calif.

[21] Appl. No.: 771,883

[22] Filed: Sep. 3, 1985

[51] Int. Cl.$^5$ .................... C12P 21/00; C12N 1/06; C12N 1/02

[52] U.S. Cl. ................... 435/71.2; 435/259; 435/261; 435/800; 435/839; 435/849; 435/875

[58] Field of Search ............. 435/68, 259, 261, 800, 435/803, 804, 849, 839, 875, 71.2

[56] References Cited

U.S. PATENT DOCUMENTS 4,560,491 12/1985 Sherman ........................ 422/28

FOREIGN PATENT DOCUMENTS 0061250 9/1982 European Pat. Off. ............ 435/259

OTHER PUBLICATIONS

Akers, Considerations in Selecting Antimicrobial Preservative Agents for Parenteral Product Development, Pharmaceutical Technology, 36–46, May 1984.

Merck Index, 10th Edition (1983).

Wang and Kowal, Review of Excipients and pH's for Parenteral Products Used in the United States, J. Parenteral Drug Association, vol. 34, No. 6, pp. 452–462 (Nov.–Dec. 1980).

Wetzel, et al., Production of Biologically Active $N^\alpha$-Desacetylthymosin $\alpha_1$ in *E. coli* through Expression of Chemically Synthesized Gene, Biochemistry, 19, 6096–6104 (1980).

*Primary Examiner*—Elizabeth C. Weimar
*Assistant Examiner*—Charles L. Patterson, Jr.

[57] ABSTRACT

In processes for recovery of biologically active polypeptides from fermentation cultures of recombinant host organisms, cell death is frequently a prerequisite for isolation processing of the recombinant product outside the fermentation vessel. Disclosed are improved methods for effecting efficient host cell death inside the fermentation vessel through uniformly contacting host cells in culture with microbicidal concentrations of benzyl alcohol. Illustratively, *E. coli, B. subtilis,* and *P. aeruginosa* cultures are advantageously treated with from 0.5 to 10.0% (v/v) of benzyl alcohol in the absence of pH or temperature changes within the fermentor.

1 Claim, 1 Drawing Sheet

EFFECT OF BENZYL ALCOHOL CONCENTRATION ON KILLING OF E COLI AT 214 $OD_{600}$

EFFECT OF CELL DENSITY ON KILLING OF E COLI AT 1.6% BENZYL ALCOHOL

METHOD FOR MICROBIAL CELL KILLING

The present invention relates to processes for effecting host cell death in the initial stages of the recovery of biologically active polypeptides from recombinant host microorganisms.

Guidelines established by the National Institutes of Health (NIH) require the total containment of microorganisms manipulated by recombinant DNA (rDNA) techniques when they are grown in volumes greater than ten liters. Guidelines for Research Involving Recombinant DNA Molecules, 49 Fed. Reg. 46266 Appendix K-IV-B (1984), provides, in pertinent part, "Culture fluids . . . shall not be removed from a closed system or other primary containment equipment unless viable organisms containing recombinant DNA molecules have been inactivated by a validated inactivation procedure". This is commonly complied with by using the cell fermentor as the primary containment vessel and by killing the microbes before they are removed from the vessel for harvesting and recombinant product purification.

Many methods are currently known for killing microbial cells. Such methods involve application of heat, addition of solvents or of strong acids or bases, or the use of electricity or radiation. While the use of electrical or radiation energy may be effective for killing cell cultures on a small scale, it may not be so effective in large process scale equipment. In addition, the use of such electrical or radiation energy to kill cells on a large scale raises serious health and safety concerns for fermentation facility personnel.

Techniques calling for the application of heat or strong bases or acids (high or low pH) to cultures are generally effective in achieving complete cell kills but suffer from other limitations. The heating and subsequent cooling of cell cultures is energy intensive, requires additional capital equipment and is costly. Even more importantly, the temperatures and time periods required to ensure complete cell death are such that they give rise to degradation of microbial cell products (as by denaturation of polypeptides) and tend to hinder purification of those products. Frequently, heat-denatured polypeptides will lose their solubility and will precipitate during initial centrifugation steps. Because of higher protein content in the precipitate, higher gravitational forces during centrifugation are required to collect desired polypeptide fractions and greater extraction volumes are therefore typically required with attendant greater demand and expense for supplies, chemicals and equipment to handle such volumes. The use of centrifugation as an initial separation procedure may thus not be economical for large-scale processing.

Product degradation, denaturation of polypeptides and the associated difficulty in purification are likewise serious concerns in the use of acid or base (pH) cell kill treatments. Corrosion of the fermentor vessel and its associated equipment is an additional concern when carrying out a pH cell kill. A great deal of heat is generated during a pH cell kill. This heat and the necessity to neutralize fermentor contents following the kill requires that additional equipment, materials and labor be directed toward pH cell kill procedures.

Cell kill methods involving addition of solvents or compounds such as toluene, phenol or benzalkonium chloride are also known. In Wetzel et al.; *Biochemistry*, 19, 6096-6104 (1980), a cell kill methodology is described whereby *E. coli* cells were killed by incubation in a fermentor with 0.25% each of toluene and phenol for 30 minutes. Such techniques, however, suffer from distinct limitations. The compounds and their residues are toxic to humans and represent health and safety risks to fermentor operators as well as to consumers of recombinant products. As such, they require the use of safety measures during fermentation which complicate processing. In addition, the compounds must be completely removed from the fermentation product and that product must be thoroughly purified.

Accordingly, there continues to exist a need in the art for improved methods for achieving cell death of contained microbial cultures such that degradation of pH and temperature-sensitive recombinant products is avoided.

Such improved methods would preferably utilize materials which are relatively inexpensive and easily applied, which are not highly toxic to humans, and do not leave toxic residues, and which have relatively high flash and vapor points.

BRIEF SUMMARY

The present invention provides new, safe and highly efficient methods for effecting host cell death in processes for the recovery of biologically active polypeptides from recombinant host microorganisms. In accordance with the present invention, it has been found that the addition of small amounts of benzyl alcohol to cell cultures will effectively promote cell death so as to comply with NIH guidelines calling for total containment of rDNA manipulated microorganisms. The method constitutes a milder procedure than either heat or acid/base (pH) kill and does not operate to degrade pH or temperature sensitive recombinant products. The method requires a minimum of added equipment and expense for the benzyl alcohol does not degrade fermentation equipment and the cell kill can be conducted in the fermentor vessel. In addition, benzyl alcohol is not highly toxic to humans, does not leave a highly toxic residue and has higher flash and vapor points than other solvents commonly used for killing microbial cells. Remarkably, practice of the methods of the invention also simplifies the isolation and purification of certain recombinant products.

Benzyl alcohol is recognized by the United States Pharmacopeia as an approved antimicrobial agent for parenteral products. Akers, *Considerations in Selecting Antimicrobial Preservative Agents for Parenteral Product Development*, Pharmaceutical Technology, 36-46, May 1984, discloses that benzyl alcohol is currently present in parenteral products in concentrations as high as 10%. While benzyl alcohol has been disclosed to have toxic effects when administered in relatively high doses to human infants and immature animals, it is regarded as one of the least toxic of all available parenteral antimicrobial agents. Benzyl alcohol is also disclosed [Merck Index, 9th edition (1976)] to have a higher flash point (213° F.) than compounds such as phenol (79° F.) and toluene (6-10° F.). This makes use of benzyl alcohol less of a fire hazard in industrial settings.

In the practice of the invention benzyl alcohol is uniformly contacted with cell cultures in concentrations of from 0.5% to 10% (v/v) and will effectively kill all microbial cells in a relatively short period of time. Concentrations greater than 10% (v/v) are generally no more effective as cell kill agents than lesser amounts and tend to be less satisfactory because of greater material costs and the potential need for additional subsequent purification. The rate of cell killing will depend on cell density (the denser the cell culture, the slower the proportional rate of cell killing) and the concentration of benzyl alcohol (the lower the concentration of benzyl alcohol, the slower the rate of cell killing). Use of benzyl alcohol concentrations between about 1 and 5% (v/v) balance the competing needs for inexpensive and rapid cell kills and use of concentrations between about 2.0 and 2.5% (v/v) are most preferred. While application of benzyl alcohol at conventional fermentor temperatures of about 25–30° C. provides satisfactory results, it has been found that application at fermentor temperatures of about 20° C. or lower can provide the most effective cell kills.

It has been found that benzyl alcohol is an effective cell kill agent against a variety of microbes including strains of *Escherechia coli, Pseudomonas aeruginosa* and *Bacillus subtilis*. Other aspects and advantages of the invention will become apparent upon consideration of the following detailed description thereof wherein.

DETAILED DESCRIPTION

The novel improvement of the present invention is illustrated in the following examples which relate to the use of benzyl alcohol in a cell kill procedure.

EXAMPLE 1

In this example, the cell kill effectiveness of benzyl alcohol at varying concentrations was demonstrated. A strain of *E. coli* (K-12) was grown in a 16 liter fermentor, induced for product synthesis of interleukin-2 (IL-2) by a temperature-sensitive "runaway" expression system by raising the fermentation temperature from 30° C. to 42° C. for three hours. The culture was then concentrated in a Luria broth medium to an absorbance at 600 nm light of 214. Five aliquots (initial viability, $4 \times 10^9$ cells/ml), 3 mls total volume, were then uniformly contacted with 1.6, 1.7, 1.8, 1.9 and 2.0% (v/v) concentrations of benzyl alcohol. 100μl volumes were sampled from the aliquots at various times and were diluted one hundred times to stop the killing effect of the benzyl alcohol. Samples were mixed with soft agar and plated on Luria agar at 30° C. for 48 hours. Plates were compared with a standard set of plates containing known quantities of bacteria. From this comparison, the number of decades of killing was evaluated.

Figure 1:
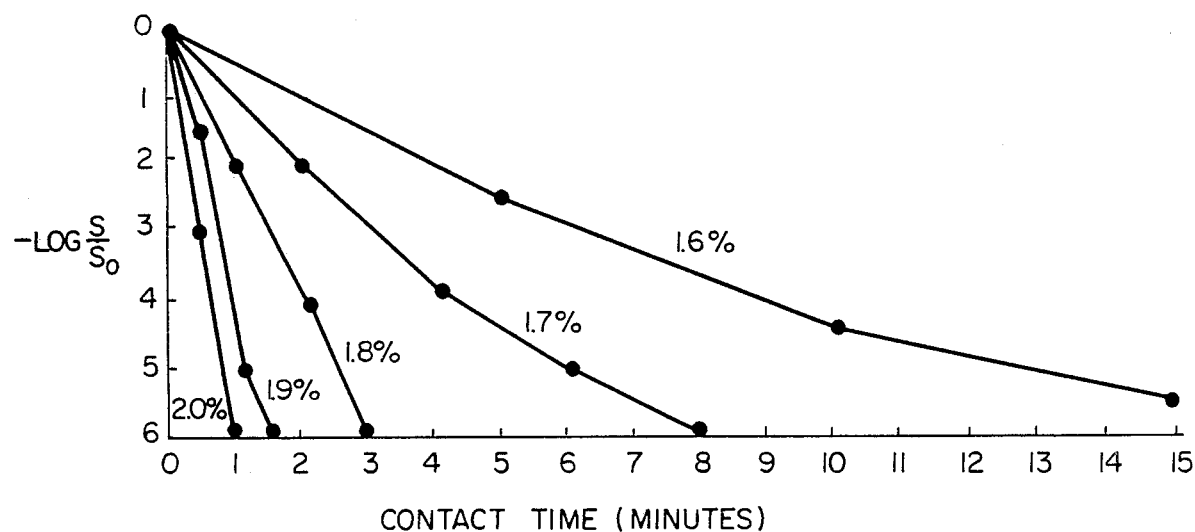
FIG. 1 illustrates a plot of the relationship between cell kill rate and benzyl alcohol contact time for various concentrations of benzyl alcohol.

FIG. 1 illustrates a plot of the relationship between cell kill rate and benzyl alcohol contact time for various concentrations of benzyl alcohol. The ordinate of the graph is the negative log of $S/S_o$ where S is the surviving bacteria at contact time t and $S_o$ is the value at contact time zero. The number $-\log (S/S_o)$ is inversely proportional to the number of surviving cells. As $-\log (S/S_o)$ increases, the number of surviving cells decreases. The plots show that the rate of cell killing is proportional to the concentration of benzyl alcohol within certain ranges, demonstrating that the benzyl alcohol killing procedure is relatively impervious to operator error. Accordingly, relatively major errors can be made in benzyl alcohol concentrations or kill times with good killing still possible over relatively short time periods and without possible damage to product, equipment or operating personnel.

EXAMPLE 2

In this example, the ability of benzyl alcohol to kill microorganisms other than *E. coli* was demonstrated. Two strains of organisms showing promise for producing rDNA derived products were tested against benzyl alcohol. Fresh overnight cultures of *Pseudomonas aeruginoda* and *Bacillus subtilis* were concentrated and viable cell counts were taken at various time intervals after being uniformly contacted with benzyl alcohol at a concentration of 2% (v/v). Virtually no living cells of either species were detectable five minutes after addition of the benzyl alcohol. The data in Table I illustrate the effectiveness of benzyl alcohol against these bacterial species.

TABLE 1

| Organism | Cell Concentration (CFU/ml) | | | |
|---|---|---|---|---|
| | 0 | 1 | 5 | 10 min |
| *Pseudomonas aeruginosa* | $1 \times 10^{11}$ | $>10^6$ | 0 | 0 |
| *Bacillus subtilis* | $3 \times 10^9$ | 13 | 0 | 0 |

EXAMPLE 3

In this example, the effect of cell density on the killing kinetics of benzyl alcohol was investigated. A strain of *E. coli* was grown in a 16 liter fermentor according to the procedure of Example 1. The culture was induced for synthesis of the alanine analogue of IL-2 and three samples were concentrated to absorbances at 600 nm light of 53.5, 107 and 214 (initial viability at $OD_{600} 214$, $4.9 \times 10^9$ cells/ml). The three samples were each uniformly contacted with benzyl alcohol at a concentration of 1.6% (v/v). 100μl volumes were taken from the samples at various times and were diluted one hundred times to stop the killing effect of the benzyl alcohol. Samples were mixed with soft agar and plated on Luria agar at 30° C. for 48 hours. Plates were compared with a standard set of plates containing known quantities of bacteria. From this comparison, the number of decades of killing was evaluated.

Figure 2:
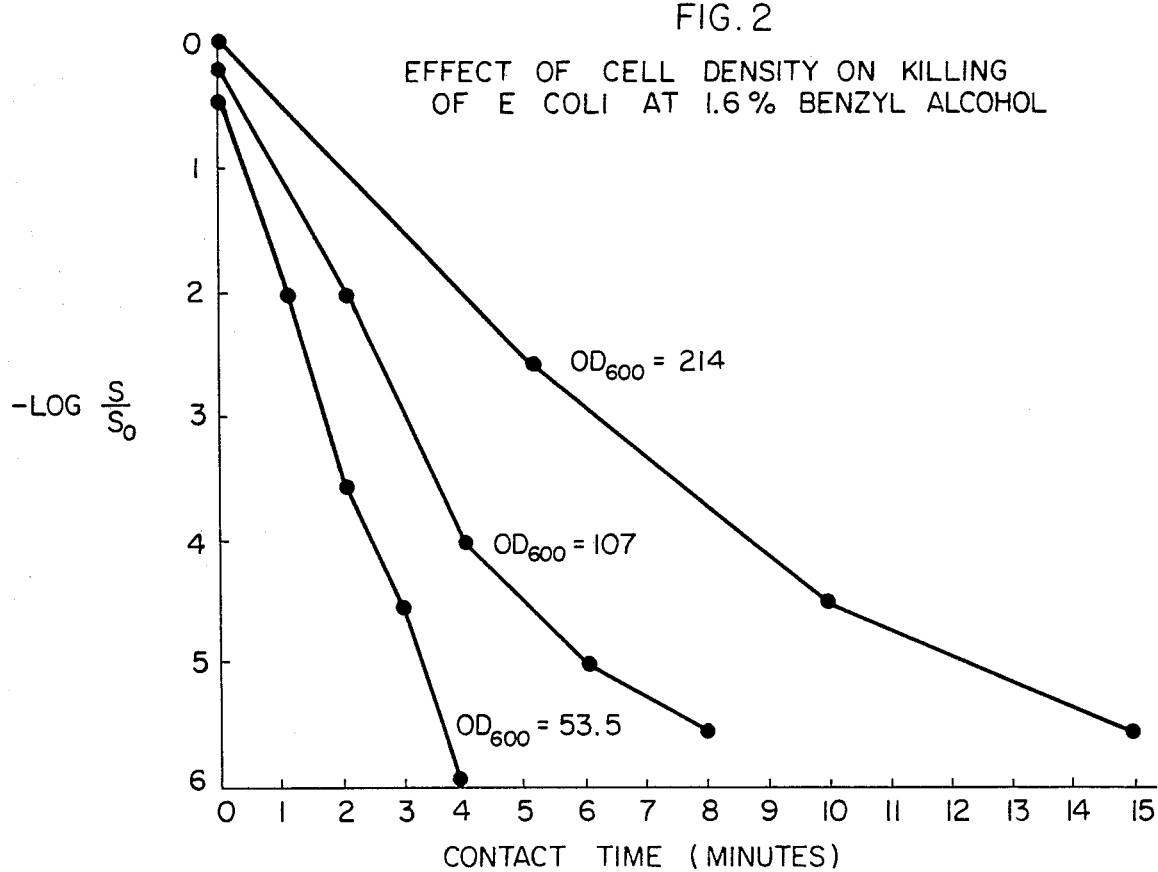
FIG. 2 illustrates a plot of the relationship between cell kill rate and benzyl alcohol contact time for cultures of varying initial cell densities.

FIG. 2 illustrates a plot of the relationship between cell kill rate and cell density for a fixed concentration of benzyl alcohol. The ordinate of the graph is the negative log of $S/S_o$ where S is the surviving bacteria at contact time t and $S_o$ is that value at contact time zero of the sample with an absorbance at 600 nm light of 214. The number $-\log (S/S_o)$ is proportional to the number of surviving cells and as $-\log (S/S_o)$ increases, the number of surviving cells decreases. The plots in FIG. 2 show that the rate of cell killing is a function of cell density at a fixed concentration of benzyl alcohol.

EXAMPLE 4

In this example, a comparison was made of benzyl alcohol with other cell killing agents with respect to ease of purification of cell products. A major step in the purification of cellular products can be made in the initial (one or more) centrifugation step(s) following cell lysis if soluble intracellular proteins are not extensively denatured (and made insoluble) in the cell killing step.

In this example, samples of a strain of *E. coli* induced for synthesis of IL-2 were subjected to killing procedures via exposure to: (1) 2.0% benzyl alcohol; (2) acid (pH 2.0); (3) 1% benzalkonium chloride; and (4) 0.5% toluene. These four samples plus a control group of live cells were lysed and centrifuged. The amount of protein was measured in both the soluble and the pelleted fractions for each cell. The percentage of protein which precipitated in each sample is give in Table II.

TABLE II

Comparison of Killing Methods with Respect to Percent Protein Precipitated

| Killing Agent | % Protein in Pellet |
| --- | --- |
| Benzyl alcohol (2.0%) | 66 |
| Acid (pH 2.0) | 83 |
| Benzalkonium Chloride (1%) | 78 |
| Toluene (0.5%) | 67 |
| Control (live cells) | 65 |

The high proportions of protein precipitated from the treatments involving acid and benzalkonium chloride indicate that these treatments denature and precipitate relatively large amounts of protein in the initial centrifugation step. In many rDNA fermentation processes the recombinant product is insoluble and is isolated from the centrifuged pellet. As previously indicated, large amounts of denatured and precipitated polypeptides can make initial purification steps significantly more difficult and expensive by increasing the amount of undesired material found in the precipitated pellet. Benzyl alcohol and toluene, however, denature relatively small amounts of polypeptide as can be seen by comparison with results from the untreated control. They neither denature significant amounts of desired polypeptide, nor do they overload the precipitate with large amounts of other degraded material. This aids in purification of the recombinant product by reducing centrifuge loadings as well as demand for supplies and chemicals. Benzyl alcohol remains superior to toluene for use in cell kills because it is easier to use operationally than toluene and is not highly toxic to humans.

EXAMPLE 5

In this example, a strain of *E. coli* was grown in a fermentor, induced for synthesis of a leukocyte interferon analog polypeptide product and concentrated in a culture medium. Samples from the culture were treated with acid or with benzyl alcohol to achieve a cell kill. The cell samples were suspended in ten volumes of 100mM Tris (pH 9) and were then dispersed with a polytron mixer. The samples were then each passed through a Gaulin homogenizer three times at 7000 psi during which greater than 95% cell breakage was achieved. The samples were then run through a centrifuge for 30 minutes at 4000 times gravity and the weight and volume of the precipitated pellet, the supernatent fluid and the protein contained therein was measured.

TABLE III

| Killing Agent | Grams of Protein in Supernatent per Kilogram Cell Paste | Grams of Protein in Pellet per Kilogram Cell Paste | % Interferon in Pellet |
| --- | --- | --- | --- |
| Benzyl Alcohol | 91 ± 5 | 59 ± 5 | >95% |
| Acid | 8 ± 5 | 142 ± 5 | >95% |

Both samples had greater than 95% of the desired polypeptide precipitate to the pellet. The cell culture sample treated with benzyl alcohol, however, had far less precipitation of undesired polypeptides than that treated by the pH method. While acid treatments have been known to denature desired polypeptides, it is believed that benzyl alcohol does not even destroy the integrity of inclusion bodies containing the recombinant interferon. Such inclusion bodies are discrete enclosed agglomerations of polypeptides. They function to concentrate and protect polypeptide products and are of value for those reasons. Benzyl alcohol appears to have an advantage of promoting cell membrane stability such that a much higher proportion of the interferon product can successfully be isolated.

Numerous modifications and variations in the invention are expected to occur to those of skill in the art upon consideration of the foregoing description. As one example, it has been preliminarily observed that the rate of *E. coli* host cell kill at a constant benzyl alcohol concentration is somewhat improved if the temperature of the fermentation broth is lowered from the typical 25-30° operating temperature range (or the 37° C. temperature typically employed for temperature-sensitive "runaway" plasmid expression systems) to about 20° C. Consequently, only such limitations as appear in the appended claims should be placed on the invention.

What is claimed is:

1. In a process for the recovery of biologically active polypeptides from fermentation cultures of recombinant host microorganisms wherein host cell death is a prerequisite for isolation processing of the recombinant product outside the fermentation vessel, an improvement in methods for effecting efficient host cell death, said improvement consisting essentially of uniformly contacting host cells selected from the group consisting of *Escherichia coli, Pseudomonas aeruginosa* and *Bacillus subtilis* in culture with microbicidal concentrations of benzyl alochol.

* * * * *